United States Patent
Lievois et al.

(10) Patent No.: US 9,002,650 B2
(45) Date of Patent: Apr. 7, 2015

(54) MULTIPHASE FLOW METER FOR SUBSEA APPLICATIONS USING HYDRATE INHIBITOR MEASUREMENT

(75) Inventors: John Lievois, Houston, TX (US); Vijay Ramakrishnan, Kingwood, TX (US); Babajide Adejuyigbe, Houston, TX (US)

(73) Assignee: Weatherford/Lamb, Inc., Houston, TX (US)

( * ) Notice: Subject to any disclaimer, the term of this patent is extended or adjusted under 35 U.S.C. 154(b) by 948 days.

(21) Appl. No.: 12/860,720

(22) Filed: Aug. 20, 2010

(65) Prior Publication Data

US 2012/0046870 A1 Feb. 23, 2012

(51) Int. Cl.
| | | |
|---|---|---|
| *G01F 1/74* | (2006.01) | |
| *G01N 21/35* | (2014.01) | |
| *G01F 1/44* | (2006.01) | |
| *G01F 1/88* | (2006.01) | |
| G01N 21/359 | (2014.01) | |
| G01N 21/3577 | (2014.01) | |

(52) U.S. Cl.
CPC ........ *G01N 21/35* (2013.01); *G01F 1/44* (2013.01); *G01F 1/74* (2013.01); *G01F 1/88* (2013.01); *G01N 21/359* (2013.01); *G01N 21/3577* (2013.01)

(58) Field of Classification Search
USPC ................ 702/12; 250/269.1, 339.12
See application file for complete search history.

(56) References Cited

U.S. PATENT DOCUMENTS

| 7,834,312 B2 | 11/2010 | Lievois et al. |
| 2007/0114372 A1* | 5/2007 | Lievois et al. ............. 250/269.1 |
| 2008/0093081 A1* | 4/2008 | Stoisits et al. ................ 166/366 |
| 2010/0193194 A1* | 8/2010 | Stoisits et al. ................ 166/335 |

FOREIGN PATENT DOCUMENTS

| WO | 01/71324 A1 | 9/2001 |
| WO | 2010/133348 A2 | 11/2010 |

OTHER PUBLICATIONS

GB Search Report for GB Application No. 1114283.3, dated Dec. 19, 2011.

\* cited by examiner

*Primary Examiner* — Jonathan C Teixeira Moffat
*Assistant Examiner* — Hien Vo
(74) *Attorney, Agent, or Firm* — Patterson & Sheridan, LLP (57) ABSTRACT

Methods and apparatus for determining phase fractions (relative concentrations) within a multiphase fluid mixture, in the presence of an injected hydrate inhibitor. Combining this phase fraction information with a hydrate inhibitor injection rate (HIIR) enables resolving oil and water flow rates for the phase fractions. The liquid flow rates and a total combined flow rate of the fluid mixture—determined based on a differential pressure of the fluid mixture through a given area—enable resolving a gas flow rate.

17 Claims, 6 Drawing Sheets

MULTIPHASE FLOW METER FOR SUBSEA APPLICATIONS USING HYDRATE INHIBITOR MEASUREMENT

BACKGROUND OF THE INVENTION

1. Field of the Invention

Embodiments of the invention generally relate to flow analysis for hydrocarbon production and, more particularly, to flow rate analysis in a multiphase fluid in the presence of a hydrate inhibitor.

2. Description of the Related Art

Oil and/or gas operators periodically measure water/oil/gas phase fractions (relative concentrations) of an overall production fluid flow in order to aid in optimizing well production, allocating royalties, inhibiting corrosion/hydrates (e.g., based on the amount of water), and generally determining the well's performance. Multiphase metering is desired for measuring individual well production of oil, water, and gas. In subsea applications, since many production systems involve commingling of multiple wells prior to the riser, subsea multiphase metering may be the only option to get individual well rates other than a measure-by-difference technique.

Various approaches for analyzing the phase fraction of such fluid flows exist and include full or partial phase separation and sensors based on capacitance, density and microwave measurements. However, known measurement techniques suffer from their own unique drawbacks and/or limitations, such as frequent calibrations, as well as sensitivity to salinity, gas, and emulsions. In addition, current subsea multiphase meters can be prohibitively expensive.

Water in gas wells introduces the prospect of hydrate formation that may impede or plug the flow and create unsafe flowing conditions. Hydrates are ice-like crystals of water and hydrocarbon (or carbon dioxide, etc.) that form at low temperatures and high pressures common in subsea applications.

Furthermore, gas wells that have a high flow rate may produce large pressure drops across chokes and other flow-area changes. At these locations, Joule-Thomson cooling can reduce temperatures significantly, which may result in severe hydrate problems in a matter of hours or even minutes if water is present. Serious problems result once the hydrates form and block or limit flow. Hence, most flow assurance methodologies are aimed at prevention of hydrate formation.

Some approaches utilize chemical injection to inhibit gas hydrate formation. However, cleaning and treatment procedures required at the surface to remove the hydrate inhibitor along with high costs of the inhibitor itself may contribute to production expenses. Therefore, injection of methanol, as an exemplary hydrate inhibitor, increases costs when done at levels beyond that required based on the water that is present. Known measurement techniques are not well-suited to make low water measurements especially when the fluid flow is further complicated by the hydrate inhibitor injection.

Therefore, there exists a need for an improved infrared optical detector and overall phase fraction measurement to enable, for example, flow assurance with improved sensitivity and accuracy, improved reservoir management, and improved allocation from a producing well. Accordingly, techniques and systems for determining the flow rates of components of a multiphase fluid containing a hydrate inhibitor are desirable.

SUMMARY OF THE INVENTION

Embodiments of the present invention generally provide methods and apparatus for determining flow rates of a fluid mixture's components using a hydrate inhibitor injection rate (HIIR).

One embodiment of the present invention is a method. The method generally includes determining an injection rate of a hydrate inhibitor, determining relative concentrations of liquids in the fluid mixture including a relative concentration of the hydrate inhibitor, and calculating flow rates of the liquids (other than the hydrate inhibitor injection rate (HIIR)) as well as a gas flow rate based on the HIIR and the relative concentrations of the liquids.

Another embodiment of the present invention provides a system. The system generally includes a well and a control unit for controlling a hydrate inhibitor injection rate (HIIR) in a fluid mixture of the well. The control unit is typically configured to determine an injection rate of a hydrate inhibitor, determine relative concentrations of liquids in the fluid mixture including a relative concentration of the hydrate inhibitor, and calculate flow rates of the liquids (other than the HIIR) as well as a gas flow rate based on the HIIR and the relative concentrations of the liquids.

Yet another embodiment of the present invention provides a computer-readable medium containing a program which, when executed by a processor, performs operations. The operations generally include determining an injection rate of a hydrate inhibitor, determining relative concentrations of liquids in the fluid mixture including a relative concentration of the hydrate inhibitor, and calculating flow rates of the liquids (other than the HIIR) as well as a gas flow rate based on the HIIR and the relative concentrations of the liquids.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

Embodiments of the invention generally relate to subsea multiphase flow meters capable of determining phase fractions (relative concentrations) within a multiphase fluid mixture, in the presence of an injected hydrate inhibitor. Combining this phase fraction information with a hydrate inhibitor injection rate (HIIR) enables resolving oil and water flow rates for the phase fractions. The liquid flow rates and a total combined flow rate of the fluid mixture—determined based on a differential pressure of the fluid mixture through a given area—enable resolving a gas flow rate.

Figure 1:
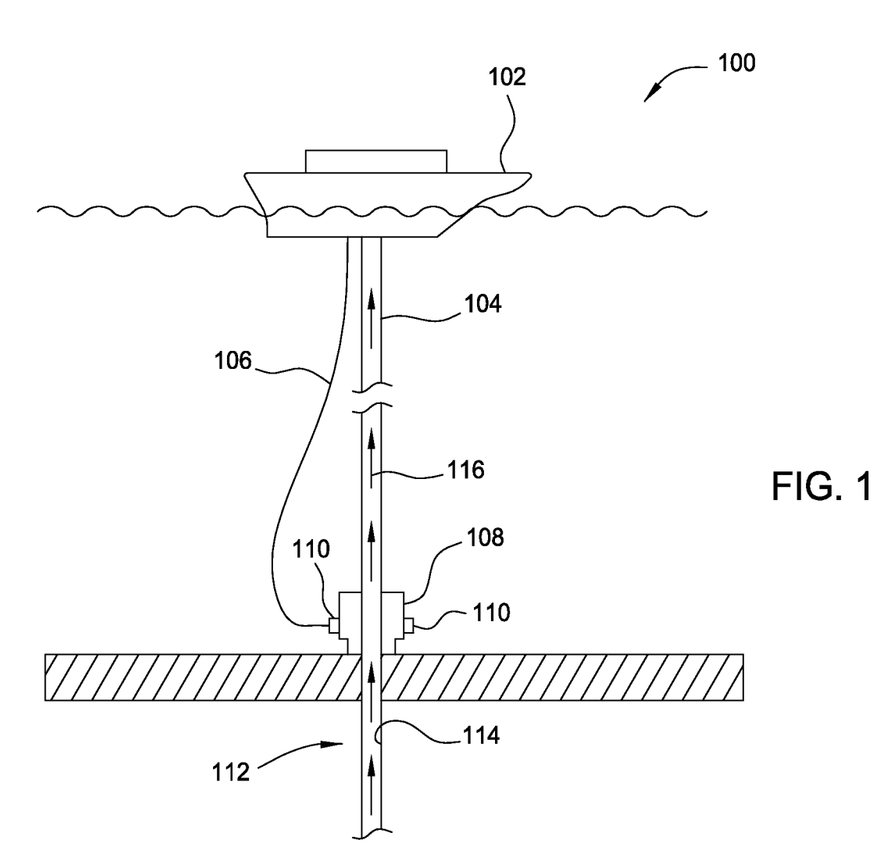
FIG. 1 is a schematic depiction of an example subsea production system with an umbilical for transmitting a hydrate inhibitor to equipment of the subsea production system to prevent, or at least significantly reduce, the formation of solids, such as hydrates, in the fluid flow, in accordance with an embodiment of the present invention.

The production of oil and/or gas with a subsea production system 100 such as that depicted in FIG. 1 is a common practice in the oil and gas industry. A riser 104 may extend from a vessel 102 at the surface of the sea to a subsea well 112 at the sea floor. It will be readily apparent to those skilled in the art that the diameter of the riser 104 may be varied as desired, to typically coincide with the inner diameter of a bore 114 of the subsea well 112 containing a fluid flow 116 as depicted by arrows. For some embodiments, the subsea production system 100 may comprise multiple subsea wells 112.

A subsea tree 108 may be disposed above the subsea well 112 and connected to create a high pressure wellhead. The subsea tree 108 may be a conventional horizontal or vertical production tree and may comprise multiple valves 110. For some embodiments, the subsea production system 100 may comprise a utility umbilical 106, wherein the umbilical 106 may contain a number of lines bundled together to provide electrical power, control, hydraulic power, fiber optics communication, chemical transportation, or other functionalities.

For some embodiments, the umbilical 106 may include a chemical injection tubing or service line for transmitting hydrate inhibitors (e.g., methanol, ethanol, or glycol) to equipment of the subsea production system 100, wherein the inhibitors may be designed and provided in order to prevent, or at least significantly reduce, the formation of solids, such as hydrates, in the fluid flow 116. For some embodiments, the hydrate inhibitor may be injected through a valve 110 of the subsea tree 108, such as a kill wing valve, wherein a hydrate inhibitor injection rate (HIIR) may be controlled.

Figure 2:
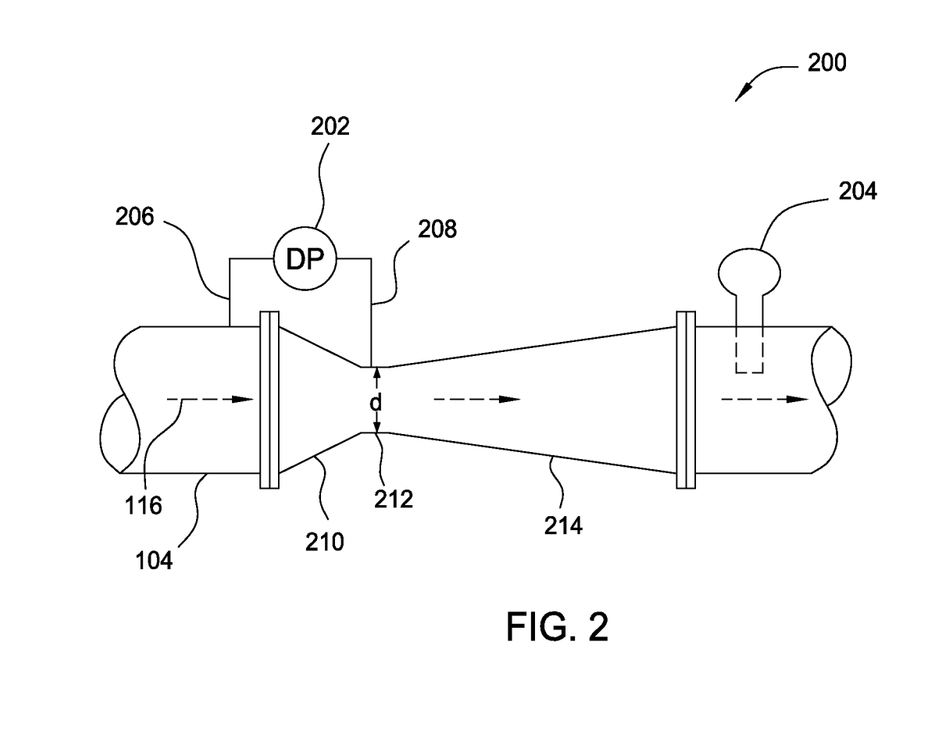
FIG. 2 is a conceptual diagram of a flow meter configuration, including a differential-pressure-based meter and an infrared optical detector which may be disposed in series with a conduit for containing a flowing fluid, in accordance with an embodiment of the present invention.

FIG. 2 illustrates a flow rate measuring system 200 comprising a Venturi-based meter 202 and an infrared optical detector 204, which may be inserted in series with the riser 104 containing a fluid flow 116 as depicted by the arrows. For some embodiments, the flow rate measuring system 200 may be disposed in series with a conduit or a pipeline further upstream or downstream and coupled to a subsea control module for controlling the well 112, e.g., by increasing or decreasing production. The infrared optical detector 204 may be positioned upstream or downstream of the Venturi-based meter 202. The flow rate measuring system 200 along with the HIIR may enable determination of individual flow rates for gas, water, and oil, as will be further discussed.

Various differential pressure devices, such as the Venturi-based meter 202, Venturi tubes, nozzles, orifice plates, and V-cones, utilize a change in flow cross-sectional area to produce changes in velocity and pressure of the fluid flow 116 according to conservation of energy and mass as the fluid flow 116 passes through such devices. Any of these differential pressure devices may therefore provide a differential pressure measurement suitable for applying in equations relating to the conservation of energy and mass in order to determine a property, such as total volume flow rate, of the fluid flow 116. Calculations shown hereinafter refer to the Venturi-based meter 202 as an example way to determine the total volume flow rate while similar modified equations may derive the same results with other ones of the differential pressure devices.

The Venturi-based meter 202 includes first and second ports 206, 208 which may be exposed to pressures of the fluid flow 116 that traverses through a converging section 210 into a throat section 212. As a further example of a different type of differential pressure device, the change in flow cross-sectional area may be brought about with a curved inlet section (as in an ISA-1932 nozzle) or with an abrupt change (as in an orifice plate) in some to create a measurable pressure difference. In some embodiments, the divergent (outlet) section 214, which aids in maximizing pressure recovery, may be designed differently or be altogether non-existent. The Venturi-based meter 202 defines a differential pressure sensing meter between the first port 206 which may be disposed upstream of the converging section 210 and the second port 208 which may be located in the throat section 212.

Figure 3:
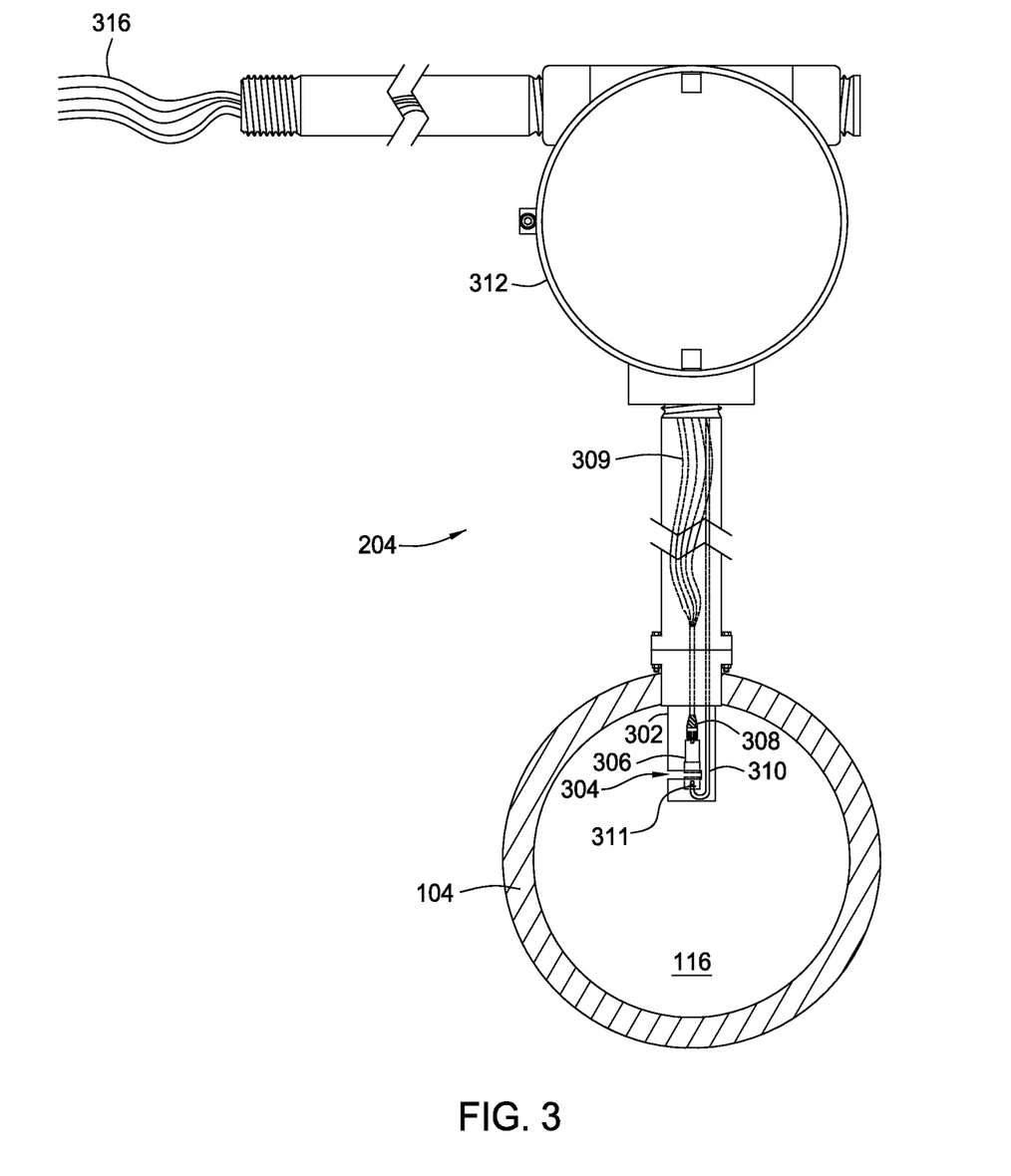
FIG. 3 is a partial section view of the infrared optical detector having a probe end inserted into the conduit, in accordance with an embodiment of the present invention.

FIG. 3 illustrates the infrared optical detector 204 disposed on the riser 104 or other conduit that carries the fluid flow 116 therein. The detector 204 may operate based on principles of spectroscopy by relying on differences in absorption between oil, water, and hydrate inhibitor of near infrared light. As a suitable example of the detector 204, U.S. Patent Publication No. 2007/0114372, which is herein incorporated by reference, describes an infrared optical fiber system capable of determining, for example, the percentages of water, oil, and hydrate inhibitor. A probe end 302 of the detector 204 may be inserted into the riser 104 such that a sampling region 304 may be preferably located near the wall of the riser 104. A body portion 312 of the detector 204 may be coupled to the probe end 302 and may house electronics (not shown) outside of the riser 104.

The detector 204 may further comprise a broad band infrared source 311 coupled to a power supply line 310 and located on an opposite side of the sampling region 304 from a collimator 306 that may be coupled to the body portion 312 by optical outputs 309 connected thereto by a common connector 308 such as a SubMiniature Version A (SMA) connector. For some embodiments, the source 311 may comprise a tungsten halogen lamp capable of emitting light in a range of wavelengths that includes particular wavelengths selected for interrogation as discussed in detail below. For other embodiments, the source 311 may comprise multiple lamps arranged adjacent to each other. Input and output wiring connections 316 may lead from the body portion 312 of the detector 204 for providing power to the detector 204 and communication with the control module, which may be located subsea for some embodiments, and on the vessel 102 for other embodiments.

Figure 4:
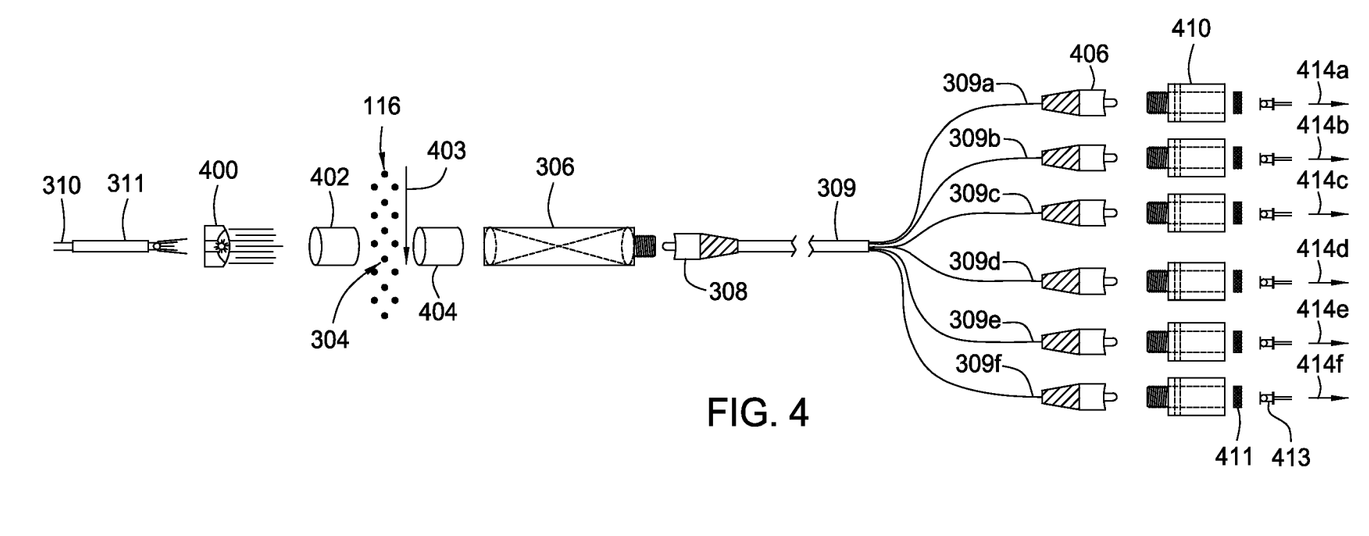
FIG. 4 is an exploded view of internal components of the infrared optical detector illustrated in FIG. 3, in accordance with an embodiment of the present invention.

FIG. 4 illustrates internal components of the infrared optical detector 204 in an exploded view. These components may comprise the source 311, a parabolic (or elliptic) reflector 400 for directing light from the source 311, first and second sapphire plugs 402, 404, the collimator 306 and the optical outputs 309 that couple the collimator 306 to infrared filters 411. An area between the sapphire plugs 402, 404 may define the sampling region 304 where fluid of the fluid flow 116 may flow across as indicated by arrow 403.

In operation, light from the source 311 may pass through the first sapphire plug 402 and through the fluid of the fluid flow 116 where the light may be attenuated prior to passing through the second sapphire plug 404. Unique absorption characteristics of the various constituents of the fluid flow 116 may cause at least some of the attenuation. The collimator 306 adjacent the second sapphire plug 404 may focus and concentrate the attenuated light into optical outputs 309 via the common connector 308. The optical outputs 309 typically comprise a multitude of optical fibers that may be divided into groups 309a-f. The exact number of fibers and/or groups formed may vary for different embodiments.

Each of the six groups 309a-f may connect to a housing 410 via a connector 406 such as an SMA connector. A photo diode 413 may produce an electrical signal proportional to the light received from a respective one of the groups 309a-f of the optical outputs 309 after passing through a respective one of the filters 411. Preferably, a logamp circuit (not shown) may measure the electrical signals to give up to five decades of range.

Each of the filters 411 may filter out all but a desired narrow band of infrared radiation. Since each of the filters 411 may discriminate for a selected wavelength band that is unique to that filter, each of the groups 309a-f may represent a different channel that may provide a total attenuation signal 414 indicative of the total attenuation of the light at the wavelengths of that particular filter. Thus, the signals 414a-f from the six channels may represent transmitted radiation at multiple different desired wavelength bands.

If only one wavelength is interrogated without comparison to other wavelengths, absorption-based attenuation associated with that one wavelength may not be readily distinguished from other non-absorption-based attenuation that may introduce errors in an absorption measurement. However, using multiple simultaneous wavelength measurements provided by the signals 414a-f from the different channels may enable non-wavelength-dependent attenuation, such as attenuation caused by common forms of scattering, to be subtracted out of the measurements.

An appropriate algorithm may remove these non-absorption background influences based on the fact that the non-wavelength-dependent attenuation may provide the same contribution at each wavelength and thence at each channel regardless of wavelength-dependent absorption. Thus, comparing the signals 414a-f from each channel at their unique wavelengths may enable correction for non-wavelength-dependent attenuation.

Additionally, selection of the filters 411 may determine the respective wavelength for each of the multiple simultaneous wavelength measurements associated with the signals 414a-f from the different channels. Accordingly, the different channels may enable monitoring of wavelengths at absorbent peaks of the constituents of the fluid flow 116, such as water absorbent peaks in addition to oil absorbent peaks, based on the wavelengths filtered. To generally increase resolution, a minute change in the property being measured may create a relatively large signal.

Since the relationship between concentration and absorption may be exponential rather than linear, large signal changes may occur in response to small concentration changes of a substance when there is a low cut or fraction of the substance being measured based on attenuation of the signal from the channel(s) monitoring the wavelengths associated with an absorbent peak of that substance. In contrast, small signal changes may occur in response to concentration changes of the substance when there is a high cut of the substance being measured by the same channel(s).

Accordingly, the different channels may provide sensitivity for the detector across a full range of cuts of the substance within the flow, such as from 0.0% to 100% phase fraction of the substance. For example, channel(s) with wavelengths at water absorbent peaks may provide increased sensitivity for low water fractions while channel(s) with wavelengths at oil absorbent peaks may provide increased sensitivity for high water fractions.

Another benefit of the multiple simultaneous wavelength measurements provided by the signals 414a-f from the different channels may include the ability to accurately calibrate the detector 204 with a small amount of pure fluid. Thus, calibration of the detector 204 need not require a reference cut.

Figure 5:
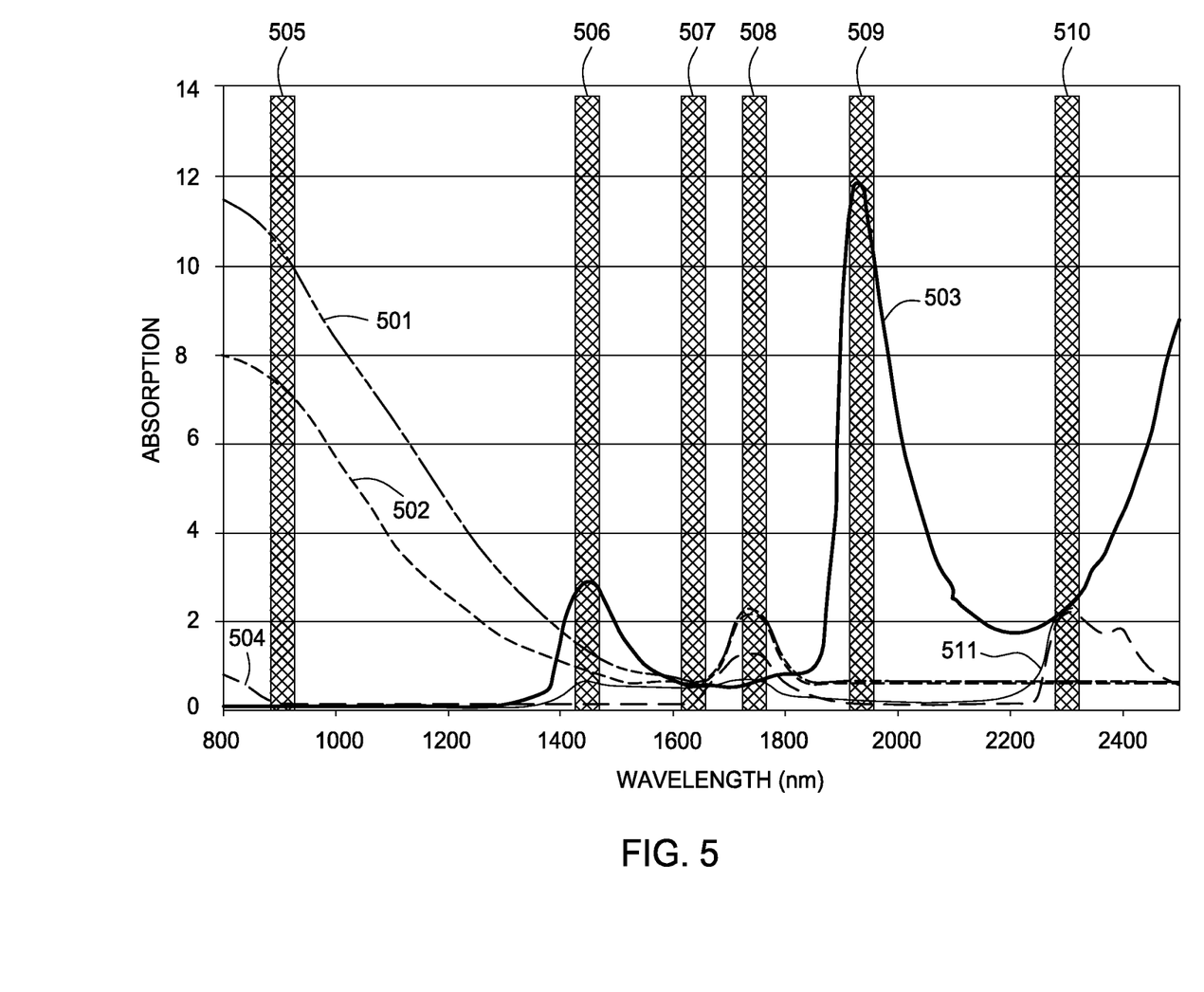
FIG. 5 is a graph illustrating absorption of two types of oil, water, condensate, and methanol for a near infrared region and wavelengths of the near infrared region selected for interrogation via channels of the infrared optical detector, in accordance with an embodiment of the present invention.

FIG. 5 illustrates a graph of absorption versus wavelength for two types of oil indicated by curves 501, 502, water represented by curve 503, condensate denoted by curve 504, and methanol denoted by curve 511, for a near infrared region. Gas provides relatively low absorption at typical test line pressures and has accordingly been omitted from the graph. Gas-based absorption is linearly related to pressure, however, so at elevated pressures accounting for the associated attenuation may improve performance. The graph shows six preferred wavelength bands 505-510 for filtering by the filters 411 in order to provide six channels of the infrared optical detector 204. Other wavelength bands may be selected without departing from the scope of the invention. The detector 204 essentially ignores salinity changes since typical salinity levels may have negligible effect on water absorption over the spectral region of interest.

In general, a first wavelength band 505 includes wavelengths within a range of approximately 900 nanometers (nm) to 1200 nm, for example about 950 nm, where there may be an oil absorbent peak. A second wavelength band 506 includes wavelengths centered around 1450 nm where there may be a water absorbent peak. A trough around 1650 nm provides another interrogation region where a third wavelength band 507 generally is centered. A fourth wavelength band 508 generally includes a peak centered about 1730 nm that may be fundamentally associated with carbon-hydrogen bonds for the two types of oil indicated by curves 501, 502 and the condensate denoted by curve 504.

Monitoring of the fifth wavelength band 509 at around 1950 nm may enable differentiation of water from any injected hydrate inhibitor used to inhibit hydrate formation since the inhibitor only has a carbon to hydroxyl bond that does not provide the same water molecule deformation that causes absorption at around 1950 nm. This ability to differentiate the inhibitor from water may permit detection of the water even during hydrate inhibitor injection. Additionally, detection of the amount of water being produced may enable determination of whether the hydrate inhibitor is sufficient given the quantity of the inhibitor selected to be injected. A sixth wavelength band 510 generally includes a peak centered around 2310 nm that may have similar absorbance for water denoted by curve 503, condensate denoted by curve 504, and methanol denoted by curve 505. The substantial similarities and/or differences in the absorption of the different phases at each of the bands 505-510 may further enable their differentiation from one another with the infrared optical detector 204.

Figure 6:
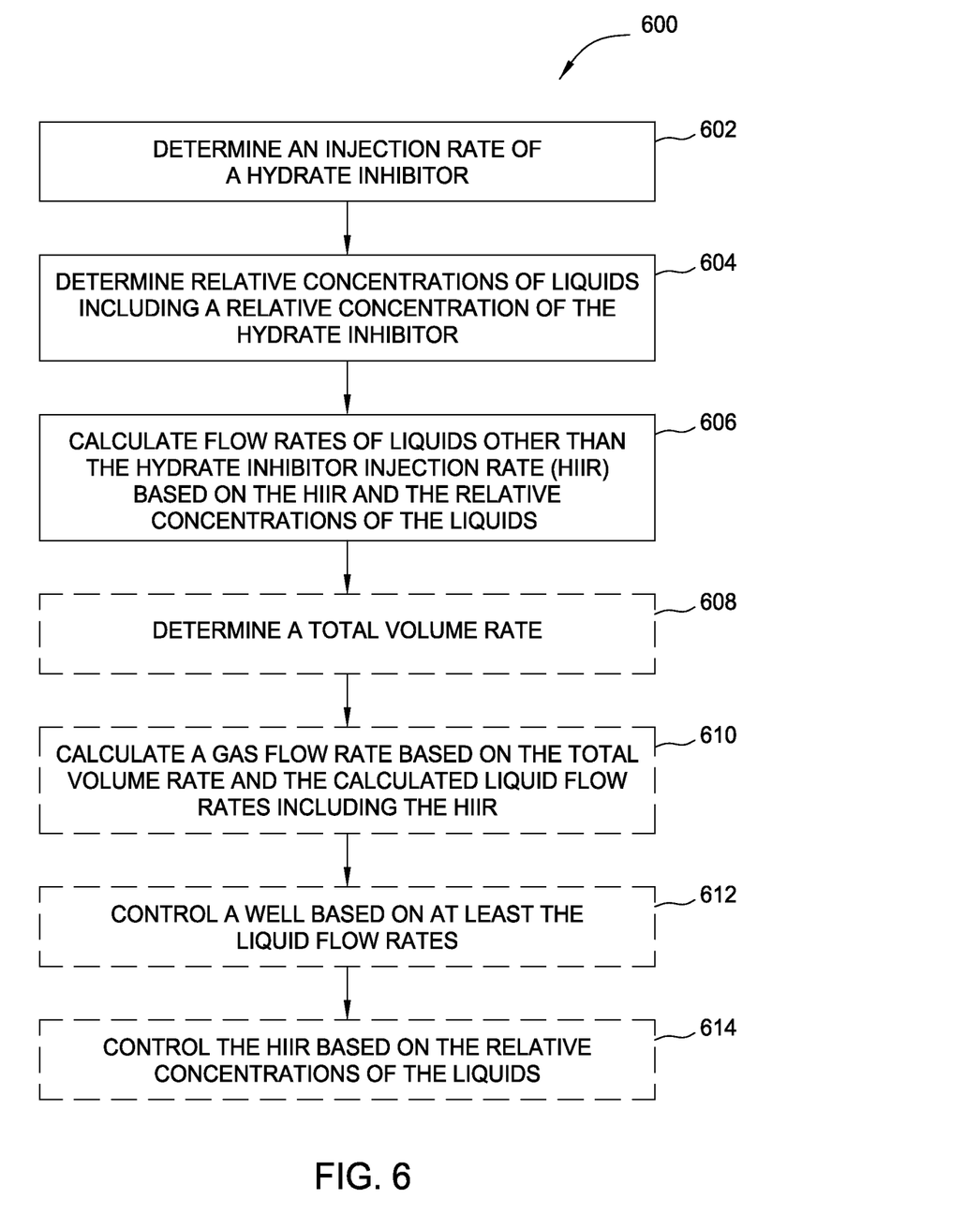
FIG. 6 is a flow chart illustrating example operations for calculating individual flow rates for gas, water, and oil in the presence of an injected hydrate inhibitor, in accordance with an embodiment of the present invention.

FIG. 6 shows a flow chart illustrating use of the infrared optical detector 204 for three phase fraction measuring along with employment of a hydrate inhibitor injection rate (HIIR) and the Venturi-based meter 202 to calculate individual flow rates for gas, water, and oil. The operations may begin at 602 by determining the HIIR. For some embodiments, the hydrate inhibitor may be injected through a valve 110 of the subsea tree 108, such as a kill wing valve. The HIIR may be determined by measuring the amount of hydrate inhibitor injected through the valve 110. For some embodiments, the HIIR may be known without measuring.

At 604, readings from the infrared optical detector 204 may enable determination of relative concentrations of liquids including a relative concentration of the hydrate inhibitor. When the detector 204 is spectroscopy-based as previously described, absorbance measurements performed may change as a function which may be defined, for example, as:

$$A_i = a_{oi}x_o + a_{wi}x_w + a_{gi}x_g + a_{hi}x_h + S \quad \text{(Equation 1)},$$

where $A_i$ is total absorbance at wavelength i and includes chemical (absorption) and physical (scattering) effects, $a_{oi}$, $a_{wi}$, $a_{gi}$, and $a_{hi}$ are absorption coefficients for oil, water, gas, and hydrate inhibitor respectively at wavelength i, $x_o$, $x_w$, $x_g$, and $x_h$ are pathlengths of oil, water, gas, and hydrate inhibitor, respectively, and S is a scatter contribution (wavelength independent) to overall absorbance. Making five or more separate absorbance measurements at five or more different wavelengths may enable solving for five unknowns ($x_o$, $x_w$, $x_g$, $x_h$, and S) in Equation 1. The relative liquid component fractions ($\alpha_o$, $\alpha_w$, $\alpha_h$) are direct functions of the component pathlengths ($x_o$, $x_w$, $x_h$) and hence can be calculated.

At 606, using the HIIR (or $Q_h$) and the liquid component fractions ($\alpha_o$, $\beta_w$, $\alpha_h$) may enable solving for an oil flow rate ($Q_o$) and a water flow rate ($Q_w$) using the following two equations having these two values as the only unknowns:

$$Q_o = \frac{\alpha_o}{\alpha_h} HIIR, \quad \text{(Equation 2)}$$

$$Q_w = \frac{\alpha_w}{\alpha_h} HIIR. \quad \text{(Equation 3)}$$

Hence the total liquid volume rate ($Q_{liq}$) may be obtained simply by adding the individual liquid component rates:

$$Q_{liq} = Q_o + Q_w + HIIR \quad \text{(Equation 4)}.$$

Optionally, in a total volume flow rate ($Q_t$) measurement step 608, the Venturi-based meter 202 may provide fluid pressure related data to enable determination of a total volume flow rate (liquid+gas) of the mixture ($Q_t$) using the following equation:

$$Q_t = \frac{K_g A_t}{\sqrt{\frac{\rho_m}{2\Delta P}}}, \quad \text{(Equation 5)}$$

where $K_g$ is a flow coefficient (determined empirically or from published data), $\Delta P$ is the measured differential pressure, $\rho_m$ is the mixture density, and $A_t$ is the flow cross-sectional area of the throat section of the Venturi-based meter 202.

Optionally, at 610, a gas flow rate ($Q_g$) may be calculated based on the total volume flow rate (from Equation 5) and the total liquid flow rate (from Equation 4) using the following equation:

$$Q_g = Q_t - Q_{liq} \quad \text{(Equation 6)},$$

and the gas fraction ($\alpha_g$) can be calculated using:

$$\alpha_g = \frac{Q_g}{Q_t}. \quad \text{(Equation 7)}$$

The Venturi-based meter 202 may rely on solving for the total volume flow rate ($Q_t$) (in Equation 5) given a mixture density ($\rho_m$) determined by the respective liquid phase fractions ($\alpha_o$, $\alpha_w$ and $\alpha_h$, measured in the relative concentration determination step 604), gas fraction, and known component densities ($\rho_g$, $\rho_w$, $\rho_h$, $\rho_g$). Calculation of $\rho_m$, due to its dependence on gas fraction, may be carried out iteratively between Equations 5, 6 and 7.

In another embodiment, the Venturi-based meter 202 may rely on solving for the total volume flow rate ($Q_t$) and the gas flow rate ($Q_g$) using equations other than Equation 5 and Equation 6—such as empirical correlations and/or published data on Venturi-based meters in multiphase-flows.

In yet another embodiment, the Venturi-based meter 202 may rely on solving for the total volume flow rate ($Q_t$) and the gas flow rate ($Q_g$) using equations other than Equation 5 and Equation 6—such as "over-reading" correlations (empirical and/or published) of Venturi-based meters 202 in wet-gas flows.

Optionally, at 612, the subsea control module may efficiently control the well 112 based on at least the liquid flow rates by increasing or decreasing production. Optionally, at 614, the HIIR may be controlled and adjusted based on the relative concentrations of the liquids, or at least of water. For some embodiments, the infrared optical detector 204 may determine a quantification or relative concentration of the water based on absorbance readings from the signals. Further, an alarm, visual output, or automated corrective action can initiate upon detecting the water so that, for example, appropriate reductions in producing rate or increase in hydrate inhibitor injections can be made. In other words, the HIIR may be reduced when the relative water concentration is low, but then increased when the relative concentrations of water increases, in an effort to prevent the formation of hydrates at 614.

While the foregoing is directed to embodiments of the present invention, other and further embodiments of the invention may be devised without departing from the basic scope thereof, and the scope thereof is determined by the claims that follow.

What is claimed is:

1. A method of determining flow rates of a fluid mixture in a conduit, comprising:
    determining an injection rate of a hydrate inhibitor;
    determining relative concentrations of liquids in the fluid mixture including a relative concentration of the hydrate inhibitor;
    calculating flow rates of the liquids other than the hydrate inhibitor injection rate (HIIR) based on the HIIR and the relative concentrations of the liquids in the conduit; and
    controlling, by a control unit, injection of the hydrate inhibitor based on a relative concentration of water in the fluid mixture.

2. The method of claim 1, further comprising determining a total volume rate of the fluid mixture.

3. The method of claim 2, further comprising calculating a gas flow rate of the fluid mixture based on the total volume rate, the calculated liquid flow rates, and the HIIR.

4. The method of claim 1, further comprising controlling a well based on at least the liquid flow rates.

5. The method of claim 1, wherein determining the relative concentrations of the liquids comprises performing absorbance measurements with an infrared optical detector.

6. The method of claim 5, wherein the infrared optical detector comprises channels for performing the absorbance measurements, wherein each channel corresponds to a wavelength band that provides an absorbent peak for a liquid in the fluid mixture.

7. The method of claim 6, wherein determining the relative concentration of the hydrate inhibitor comprises performing the absorbance measurements on one of the channels where absorbance of the hydrate inhibitor is differentiated from absorbance of the liquids other than the hydrate inhibitor.

8. A control unit for controlling a hydrate inhibitor injection rate (HIIR) in a fluid mixture of a well, wherein the control unit is configured to:
 determine an injection rate of a hydrate inhibitor;
 determine relative concentrations of liquids in the fluid mixture including a relative concentration of the hydrate inhibitor;
 calculate flow rates of the liquids other than the HIIR based on the HIIR and the relative concentrations of the liquids; and
 control injection of the hydrate inhibitor based on a relative concentration of water in the fluid mixture.

9. The control unit of claim 8, wherein the control unit is further configured to determine a total volume rate of the fluid mixture.

10. The control unit of claim 9, wherein the control unit is further configured to calculate a gas flow rate of the fluid mixture based on the total volume rate, the calculated liquid flow rates, and the HIIR.

11. The control unit of claim 8, wherein the control unit is further configured to control the well based on at least the liquid flow rates.

12. The control unit of claim 8, wherein the control unit is configured to determine the relative concentrations of the liquids by performing absorbance measurements with an infrared optical detector.

13. The control unit of claim 12, wherein the infrared optical detector comprises channels for performing the absorbance measurements, wherein each channel corresponds to a wavelength band that provides an absorbent peak for a liquid in the fluid mixture.

14. The control unit of claim 13, wherein determining the relative concentration of the hydrate inhibitor comprises performing the absorbance measurements on one of the channels where absorbance of the hydrate inhibitor is differentiated from absorbance of the liquids other than the hydrate inhibitor.

15. A non-transitory computer-readable medium containing a program for determining flow rates of a fluid mixture in a conduit which, when executed by a processor, performs operations comprising:
 determining an injection rate of a hydrate inhibitor;
 determining relative concentrations of liquids in the fluid mixture including a relative concentration of the hydrate inhibitor;
 calculating flow rates of the liquids other than the hydrate inhibitor injection rate (HIIR) based on the HIIR and the relative concentrations of the liquids; and
 controlling injection of the hydrate inhibitor based on a relative concentration of water in the fluid mixture.

16. The computer-readable medium of claim 15, the operations further comprising:
 determining a total volume rate of the fluid mixture; and
 calculating a gas flow rate of the fluid mixture based on the total volume rate, the calculated liquid flow rates, and the HIIR.

17. The computer-readable medium of claim 15, the operations further comprising controlling a well based on at least the liquid flow rates.

* * * * *